(12) United States Patent
Cordonnier et al.

(10) Patent No.: US 6,422,066 B1
(45) Date of Patent: Jul. 23, 2002

(54) SENSOR CAPSULE FOR $CO_2$ SENSOR

(75) Inventors: Michael J. Cordonnier; H. Ping Wu, both of Beavercreek; Robert B. Spokane, Bellbrook; Jamie N. Lussier, Yellow Springs, all of OH (US)

(73) Assignee: Yellow Spring Optical Sensor Co. PLL, Yellow Springs, OH (US)

( * ) Notice: Subject to any disclaimer, the term of this patent is extended or adjusted under 35 U.S.C. 154(b) by 0 days.

(21) Appl. No.: 09/807,177

(22) PCT Filed: Oct. 29, 1999

(86) PCT No.: PCT/US99/25506

§ 371 (c)(1),
(2), (4) Date: Apr. 6, 2001

(87) PCT Pub. No.: WO00/26655

PCT Pub. Date: May 11, 2000

Related U.S. Application Data

(60) Provisional application No. 60/106,528, filed on Oct. 31, 1998.

(51) Int. Cl.[7] .................. G01N 21/64; G01N 33/52; G01N 33/553; G02B 6/00; C12M 1/40

(52) U.S. Cl. ............ 73/53.01; 73/19.1; 73/31.05; 73/23.31; 73/61.48; 73/64.47; 422/82.05; 422/82.08; 422/94

(58) Field of Search ............ 73/19.12, 19.01, 73/19.1, 53.01, 61.71, 61.48, 61.41, 61.63, 61.72, 31.05, 61.44–61.73, 64.47–64.56, 23.31; 422/82.05, 82.07, 82.08, 82.09

(56) References Cited

U.S. PATENT DOCUMENTS

| | | | |
|---|---|---|---|
| 4,003,707 A | 1/1977 | Lubbers et al. ......... 23/232 R |
| 4,198,851 A | 4/1980 | Janata ..................... 73/23 |
| 4,343,768 A | 8/1982 | Kimura .................... 422/97 |
| 4,422,129 A | 12/1983 | Briant et al. ............. 361/433 |
| RE31,879 E | 5/1985 | Lubbers et al. .......... 436/133 |
| 4,557,900 A | 12/1985 | Heitzmann ............... 422/55 |
| 5,141,873 A | 8/1992 | Steudle et al. ........... 436/148 |
| 5,244,636 A | 9/1993 | Walt et al. ............... 422/82.07 |
| 5,252,494 A | 10/1993 | Walt ....................... 436/528 |
| 5,506,148 A | 4/1996 | Munkholm ............... 436/111 |
| 5,608,167 A | 3/1997 | Hale et al. ............... 73/715 |
| 5,640,470 A * | 6/1997 | Iyer et al. ................ 385/12 |
| 5,710,012 A | 1/1998 | Nikolyukin et al. ...... 435/28 |
| 5,714,121 A | 2/1998 | Alderete et al. ......... 422/82.07 |
| 5,856,175 A | 1/1999 | Thorpe et al. ........... 435/287.5 |
| 5,866,433 A | 2/1999 | Schalkhammer et al. .. 436/525 |
| 5,889,195 A | 3/1999 | Kaneblei ................. 73/19.12 |
| 5,922,530 A * | 7/1999 | Yu .......................... 435/4 |
| 5,961,924 A * | 10/1999 | Reichert et al. ......... 422/82.11 |
| 5,985,217 A * | 11/1999 | Krulevitch et al. ...... 422/99 |
| 6,007,778 A * | 12/1999 | Cholewa .................. 422/82.05 |
| 6,030,827 A * | 2/2000 | Davis et al. ............. 435/287.1 |
| 6,045,756 A * | 4/2000 | Carr et al. ............... 422/88.11 |
| 6,096,258 A * | 4/2000 | Inbar ...................... 422/56 |
| 6,232,114 B1 * | 5/2001 | Coassin et al. .......... 435/288.4 |
| 6,277,651 B1 * | 8/2001 | Groger et al. ............ 436/518 |
| 6,312,961 B1 * | 11/2001 | Voirin et al. ............. 436/518 |

* cited by examiner

*Primary Examiner*—Hezron Williams
*Assistant Examiner*—David J. Wiggins
(74) *Attorney, Agent, or Firm*—Thompson Hine LLP

(57) ABSTRACT

A sensor capsule to facilitate positioning of an analyte sensitive element such as a $CO_2$ sensor at the end of a fiber optic probe, which discloses a dye layer defined by a dye well, fluorescent dye solution and apertures formed in a silicone sensor membrane. A TEFLON® covering membrane is positioned over the silicone membrane to retain the dye layer within the well, and perforated metal disc is positioned beneath the silicone membrane to provide support and resist swelling of the dye layer. The perforated metal disc, silicone membrane and TEFLON® membrane define a sandwich sensor structure which is positioned within an outer housing. An insert member is positioned over the sandwich sensor structure and is snap fit into outer housing to provide a sensor capsule which may be removeably positioned/replaced in association with a probe tip used for forming the fiber optic $CO_2$ SENSOR.

12 Claims, 3 Drawing Sheets

SENSOR CAPSULE FOR CO₂ SENSOR

This application is a 371 of PCT/US99/25506 filed Oct. 29, 1999 which claims benefit of Prov. No. 60/106,528 filed Oct. 31, 1998.

BACKGROUND OF THE INVENTION

1. Field of the Invention

The present invention relates generally to instruments for measuring the concentration of a gas in a fluid and more particularly relates to an improved sensor including a sensor capsule for facilitating positioning an analyte sensitive element at the end of an optical fiber probe.

2. Description of Related Art

Various forms of analyte measuring instruments have been designed and developed for use in numerous medical and industrial applications. Among these devices are those that rely on optical properties of a sensing element containing a dye which is responsive to a particular analyte. When the dye interacts with the analyte the dye undergoes an optical change, such as a change of fluorescence, which is measurable and is directly related to the concentration of the analyte contained in the medium being sampled.

The analyte sensitive substance or indicator is located in a sensor element typically including a permeable membrane allowing the analyte to permeate and interact with the indicator. The indicator, typically a dye solution. has in prior devices been held trapped between the permeable membrane and an optical sensing surface, for example. the end of a probe, and has required a dye retaining mesh. A recognized need in the use of these sensors is the ability to interchange the element containing the indicator. It is desirable to change the element containing the indicator for various reasons. including to avoid transfer of contamination when the sensor probe is applied to different sensing locations, or due to the dye leaching out of the sensor. or for other reasons which make it desirable to interchange sensor elements.

SUMMARY OF THE INVENTION

The present invention provides a sensor capsule for use in combination with a fiber optic sensor. In particular, the present invention is specifically designed for use in a carbon dioxide sensor.

The sensor capsule comprises a two-piece snap together cap including an outer housing portion and an inner insert portion which fits within the housing portion. The housing and insert portions cooperate to retain a perforated metal disc. a sensor membrane, a covering membrane and a sandwiched dye layer at a predetermined position within the sensor capsule.

The sensor membrane comprises a silicone membrane positioned in engagement with the perforated metal disc and includes an indentation defining a dye well containing an indicator dye solution. The covering membrane comprises a TEFLON (polytetrafluoroethylene) membrane positioned over the silicone membrane to retain the dye solution within the dye well.

The snap together design of the sensor capsule assembly holds the sandwiched dye layer in a rigid structure which facilitates attachment to and detachment from a sensor probe while protecting the dye layer.

Therefore, it is an object of the present invention to provide a sensor capsule for facilitating mounting of an indicator element to a sensor probe.

It is a further object of the invention to provide a sensor capsule which includes sandwiched layers for retaining a dye solution.

It is yet another object of the invention to provide a sensor capsule which provides a rigid housing for enclosing a sandwiched dye layer.

Other objects and advantages of the invention will be apparent from the following description, the accompanying drawings and the appended claims.

DETAILED DESCRIPTION OF THE PREFERRED EMBODIMENT

Figure 1:
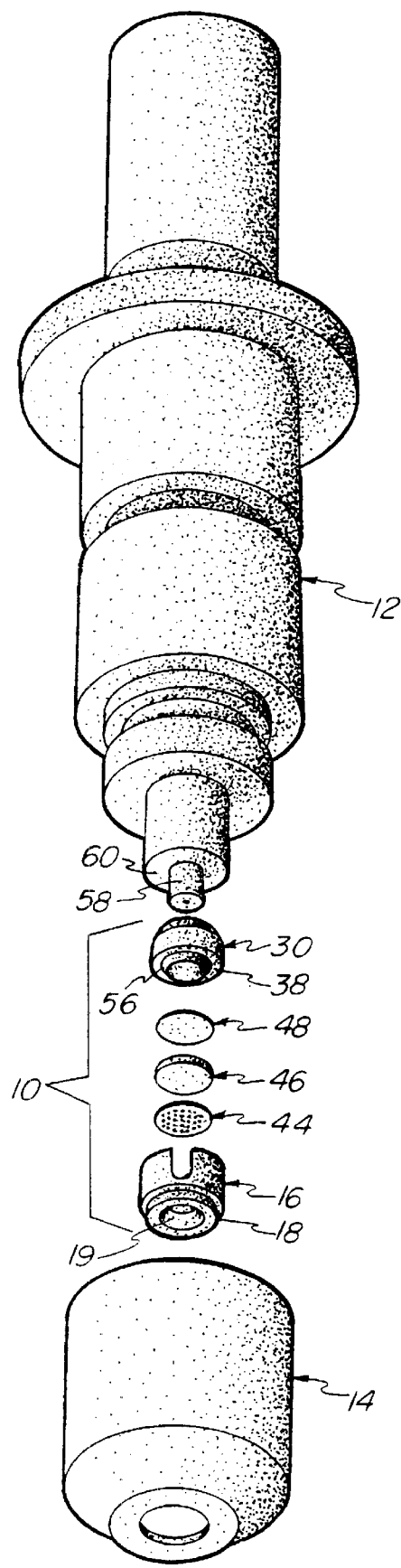
FIG. 1 is an exploded perspective view showing a probe assembly incorporating the sensor capsule of the present invention.

Referring initially to FIG. 1. the present invention provides a sensor capsule 10 which is adapted to fit on a probe housing 12 where it is held in place by a probe cap 14 positioned over the sensor capsule 10 and mounted to the housing 12. The probe housing 12 is of the type which is used with a fiber optic sensor system wherein fiber optic elements are used to transmit and detect light to and from a fluorescent dye indicator for measuring the concentration of an analyte, such as carbon dioxide.

Figure 2:
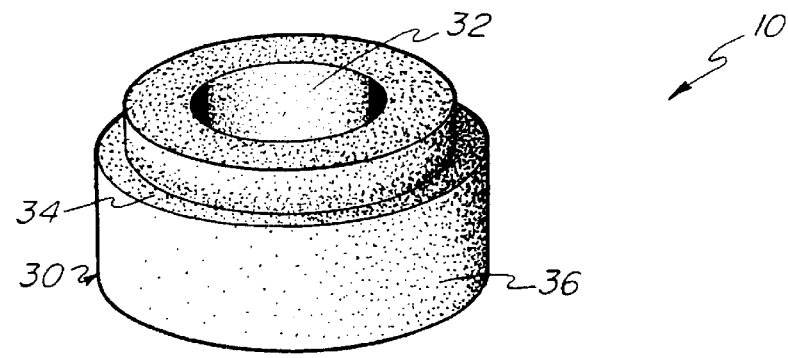
FIG. 2 is an exploded perspective view of the sensor capsule.
Figure 2:
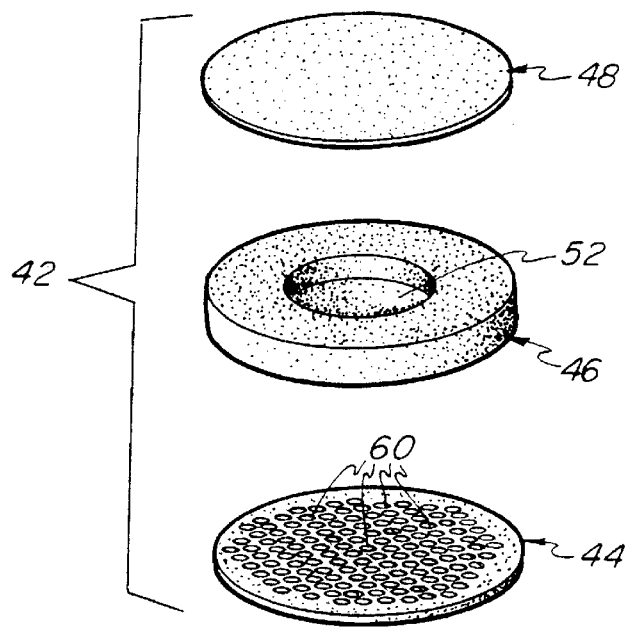
Figure 2:
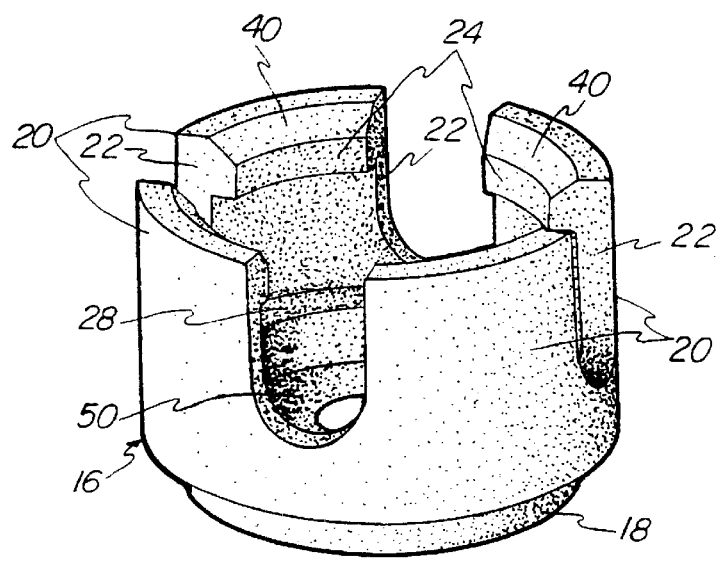
Figure 3:
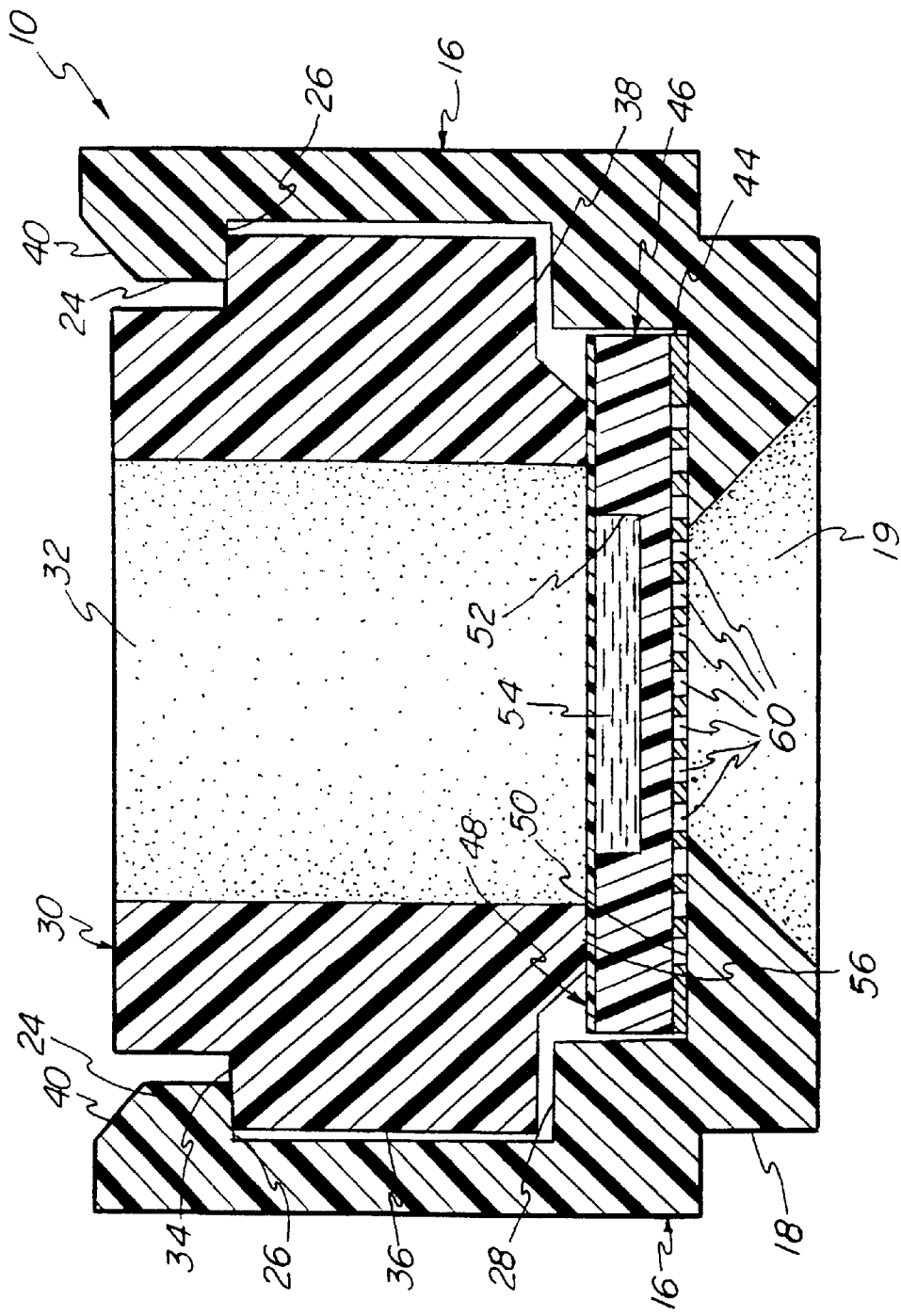
FIG. 3 is a cross-sectional elevational view of the assembled sensor capsule.

Referring further to FIGS. 2 and 3. the present invention is particularly directed to a self-contained structure defined by the sensor capsule 10 whereby the indicator or sensor dye may be conveniently brought into association with the probe housing 12 or interchanged with a different sensor capsule 10. The sensor capsule 10 comprises an outer housing 16 formed with a circular base portion 18 defining a base aperture 19. and four axially extending side walls 20 which are separated by slots 22. The distal ends of each of the side walls 20 includes a radially inwardly extending detent portion 24 having lower sides 26 located in axially spaced relation to an annular ledge 28 defined on the annular base portion 18 adjacent to a proximal end of the side walls 20.

The sensor capsule 10 further includes a cylindrical, inner insert member 30 defining an aperture 32 therethrough. In addition, an annular grooved or recessed area 34 is defined at one end of the insert member 30 extending radially inwardly from an outer surface 36 of the insert member 30. The insert member 30 is adapted to be positioned within the outer housing 16, with an annular lower surface 38 of the insert member 30 located adjacent to ledge 28 and the recessed area 34 engaged by the lower surfaces 26 of the detent portions 24. Further, it should be noted that the outer housing 16 is formed such that the side walls 20 will flex outwardly as the insert member 30 is inserted, and the detent portions 24 will snap over the recessed 34 when the insert member 30 reaches its final position to thereby positively retain the insert member 30 within the outer housing 16. Also. in order to facilitate insertion of the insert member 30, the upper surfaces of the detent portions 24 are provided with inwardly and downwardly angled portions 40 which facilitate outward flexing of the side walls 20.

The outer housing 16 and insert member 30 cooperate to hold a sandwiched sensor structure 42 comprising a perforated metal disc 44, a silicone sensor membrane 46 and a TEFLON® covering membrane 48. The perforated metal disc 44 is supported on a ledge 50 inside the outer housing 16, and the silicone membrane 46 is supported on top of the perforated disc 44. The silicone membrane 46 includes a dye well 52 containing a fluorescent dye solution 54. The TEFLON® membrane 48 acts to retain the dye solution 54 within the dye well 52.

When the perforated metal disc 44, silicone membrane 46, dye solution 54 and TEFLON® membrane 48 are positioned within the outer housing 16, and the insert member 30 is snapped into place, a lower end 56 of the insert member 30 engages the TEFLON® membrane 48 and rigidly retains the sandwiched sensor structure 42 in position at the lower end of the outer housing 16 whereby the dye solution 54 is physically retained between the silicone membrane 46 and TEFLON® membrane 48 through cooperation of the outer housing 16 and insert member 30.

When placed on the probe housing 12, a tip 58 of the probe housing 12 extends through the aperture 32 of the insert member 30 of the TEFLON® membrane 48, and the dye well 52 defines the optical path for the sensor. This optical path structure is in contrast to the typical prior art sensors which generally require a dye retaining mesh and wherein the dye solution may be trapped between a membrane and the optical sensing surface itself. Plus, the present invention retains the dye solution 54 in such a way that it may be positioned adjacent to the sensor surface at the tip 58, or easily removed for use in combination with a different probe housing 12 or to be replaced by a different sensor capsule 10. It should also be understood that compression of the silicone membrane 46 is independent of the tolerances of the fit between the probe housing 12 and the probe cap 14 in that a shoulder 60 of the probe tip 58 rests in engagement with the distal ends of the side walls 20, and the boundaries of the dye layer formed by the dye solution 54 within the dye well 52 are defined between the perforated metal disc 44 and the end of the probe tip 58 positioned at the TEFLON® membrane 48. In this manner, it is possible to construct the sensor capsule 10 such that the compression of the silicone membrane 30 is consistent from one sensor to another.

In the specific embodiment of the present invention, the outer housing 16 and insert member 30 are formed of PEEK (polyether-ether-ketone), which is a steam sterilizable USP Class VI plastic. The perforated metal disc is made of 0.005" thick 316 stainless steel having perforation holes 60 with a diameter of 0.010" spaced apart with 0.015" on-center spacing. The silicone membrane 46 is injection molded with a wall thickness of 0.025" and a well thickness or depth of 0.010", and is preferably black to prevent transmission of light therethrough. The TEFLON® membrane 48 is formed 0.002" thick, and the dye solution constrained between the TEFLON® membrane 48 and the silicone membrane 46 is a measured amount of photo-reactive HPTS (hydroxypyrene-trisulfonate) dye in a buffered solution. The perforated metal disc 44 serves as a mechanical constraint for swelling of the dye layer 54 as well as providing a short diffusion path for dissolved $CO_2$ to penetrate through. Further, the present design reduces the length of the diffusion path by 80% in comparison to prior art sensors, which feature helps to reduce the response time of the sensor.

From the above description, it should be apparent that the present invention provides certain advantages over prior art sensors including:

1. A sandwiched dye layer in a dye well;
2. A dye well defining the optical path of the sensor and eliminating the need for a dye retaining mesh;
3. A perforated metal support for the outer or silicone membrane wherein the perforated metal and the probe tip provide two solid surfaces confining the boundaries of the sandwiched dye layer;
4. A snap together cap design which facilitates assembly and which eliminates the need for 0-ring seals found in prior art sensors wherein the snap together design holds the sandwiched dye layer assembly in a rigid structure;
5. A structure providing membrane compression which is independent of the geometric tolerances of the probe housing containing the probe tip and the probe cap wherein the outer housing of the sensor capsule rests against the shoulder of the probe tip; and
6. The provision of a sensor capsule which is interchangeable for mounting on multiple probe housings.

While the form of apparatus herein described constitutes a preferred embodiment of this invention. it is to be understood that the invention is not limited to this precise form of apparatus. and that changes may be made therein without departing from the scope of the invention which is defined in the appended claims.

What is claimed is:

1. An optical sensor for measuring the concentration of an analyte in a solution, the sensor comprising:
   a sensor membrane diffusible to an analyte to be measured;
   an indentation defining a well in said sensor membrane;
   a photo-reactive dye solution located in said well and defining a dye layer; and
   a covering membrane positioned over said well to retain said dye solution in the well.

2. The sensor of claim 1 further including a thin perforated element supporting said sensor membrane, said thin perforated element defining a diffusion path for passage of said analyte to said sensor membrane.

3. The sensor of claim 2 further including a housing and an insert member wherein said covering membrane, dye solution, sensor membrane, and thin perforated element are stacked in order within said housing and sandwiched between said insert member and said housing.

4. The sensor of claim 3 wherein said insert member cooperates with said housing in a snap fit to retain said insert within said housing.

5. The sensor of claim 3 wherein said insert member includes an aperture for receiving a tip of a fiber optic probe therein.

6. The sensor of claim 2 wherein said thin perforated element comprises a stainless steel member having a plurality of perforations.

7. The sensor of claim 1 wherein said sensor membrane comprises silicone.

8. The sensor of claim 1 wherein said covering membrane comprises polytetrafluoroethylene.

9. The sensor of claim 1 wherein said dye solution comprises photo-reactive hydro-phosphoric-telluric sulfide dye.

10. An optical sensor for measuring the concentration of $CO_2$ in an analyte solution, the sensor comprising:
    a silicone sensor membrane through which $CO_2$ can diffuse and be measured;
    an indentation defining a well in said sensor membrane;
    a photo-reactive dye solution located in said well and defining a dye layer; and
    a covering membrane positioned over said well to retain said dye solution in said well.

11. The sensor of claim 10 wherein the dye solution contains a photo-reactive hydro-phosphoric-telluric sulfide dye.

12. The sensor of claim 11 wherein the covering membrane is a polytetrafluoroethylene membrane.

* * * * *